US010899725B2

(12) United States Patent
Chheda et al.

(10) Patent No.: US 10,899,725 B2
(45) Date of Patent: Jan. 26, 2021

(54) PROCESS FOR THE RECOVERY OF FURFURAL

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/346,264

(22) PCT Filed: Oct. 30, 2017

(86) PCT No.: PCT/US2017/058942
§ 371 (c)(1),
(2) Date: Apr. 30, 2019

(87) PCT Pub. No.: WO2018/085179
PCT Pub. Date: May 11, 2018

(65) Prior Publication Data
US 2019/0256484 A1 Aug. 22, 2019

Related U.S. Application Data

(60) Provisional application No. 62/415,531, filed on Nov. 1, 2016.

(51) Int. Cl.
*C07D 307/50* (2006.01)
*B01D 3/10* (2006.01)
(Continued)

(52) U.S. Cl.
CPC ............. *C07D 307/50* (2013.01); *B01D 3/10* (2013.01); *B01D 11/028* (2013.01); *B01D 11/0288* (2013.01); *C07D 307/48* (2013.01)

(58) Field of Classification Search
CPC .................................................... C07D 307/50
(Continued)

(56) References Cited

U.S. PATENT DOCUMENTS 2,078,241 A 4/1937 Fulmer et al.
2,536,732 A 1/1951 Dunlop
(Continued)

FOREIGN PATENT DOCUMENTS

CN 104387346 A * 3/2015 ........... C07D 307/48
EP 1727890 A1 12/2006
(Continued)

OTHER PUBLICATIONS

International Search Report and Written Opinion received for PCT Patent Application No. PCT/US2017/058942, dated Jan. 19, 2018, 9 pages.
(Continued)

*Primary Examiner* — Daniel R Carcanague

(57) ABSTRACT

Disclosed is a process for the extraction of furfural. The process includes subjecting a composition comprising furfural, water, at least one acid and an aromatic solvent, with a boiling point higher than that of furfural, to a first separation step in a first liquid-liquid separator providing a first organic phase and a first aqueous phase; conveying the first organic phase along a first line to a distillation column and subjecting the first organic phase to a distillation step providing a top stream comprising furfural and a bottom stream comprising the aromatic solvent; subjecting the first aqueous phase and a portion of the bottom stream to a second separation step providing a second organic phase; conveying the second organic phase along a second line which either feeds its contents into the first line or into the distillation column and subjecting the resultant mixture to said distillation step.

10 Claims, 1 Drawing Sheet

(51) Int. Cl.
    *B01D 11/02* (2006.01)
    *C07D 307/48* (2006.01)
(58) Field of Classification Search
    USPC .......................................................... 549/490
    See application file for complete search history.

(56) References Cited

U.S. PATENT DOCUMENTS

| | | |
|---|---|---|
| 3,549,319 A | 12/1970 | Wilson et al. |
| 4,409,032 A | 10/1983 | Paszner et al. |
| 4,461,648 A | 7/1984 | Foody |
| 4,533,743 A | 8/1985 | Medeiros et al. |
| 5,536,325 A | 7/1996 | Brink |
| 5,789,210 A | 8/1998 | Ho et al. |
| 5,820,687 A | 10/1998 | Farone et al. |
| 6,475,768 B1 | 11/2002 | Otero et al. |
| 7,741,084 B2 | 6/2010 | Viitanen et al. |
| 7,741,119 B2 | 6/2010 | Viitanen et al. |
| 7,781,191 B2 | 8/2010 | Dunson, Jr. et al. |
| 8,168,807 B2 | 5/2012 | Wabnitz et al. |
| 8,466,242 B2 | 6/2013 | Geremia et al. |
| 10,005,749 B2 * | 6/2018 | Chheda ............... C07D 307/50 |
| 10,087,160 B2 * | 10/2018 | Chheda ............... C07D 307/50 |
| 10,093,639 B2 * | 10/2018 | Chheda ............... C07D 307/50 |
| 10,138,218 B2 * | 11/2018 | Chheda ............... C07D 307/46 |
| 10,253,009 B2 * | 4/2019 | Chheda ............... C07D 307/48 |
| 10,479,773 B2 * | 11/2019 | Chheda ............... C07D 307/50 |
| 10,501,430 B2 * | 12/2019 | Chheda .................... B01D 3/36 |
| 10,562,874 B2 * | 2/2020 | Chheda ............... C07D 307/50 |
| 10,584,107 B2 * | 3/2020 | Chheda ............... C07D 307/48 |
| 2003/0162271 A1 | 8/2003 | Zhang et al. |
| 2009/0061490 A1 | 3/2009 | Edwards et al. |
| 2010/0019191 A1 | 1/2010 | Hoffer et al. |
| 2010/0312028 A1 | 12/2010 | Olson et al. |
| 2012/0107887 A1 | 5/2012 | Chheda et al. |
| 2012/0122152 A1 | 5/2012 | Blackbourn et al. |
| 2012/0157697 A1 | 6/2012 | Burket et al. |
| 2012/0302765 A1 | 11/2012 | Dumesic et al. |
| 2013/0295629 A1 | 11/2013 | Weider et al. |
| 2014/0018555 A1 | 1/2014 | De Vries et al. |
| 2014/0107355 A1 | 4/2014 | Dumesic et al. |
| 2019/0263767 A1 * | 8/2019 | Chheda ............... C07D 307/50 |
| 2019/0270716 A1 * | 9/2019 | Chheda ............... C07D 307/48 |
| 2019/0276422 A1 * | 9/2019 | Chheda .................... B01D 3/36 |

FOREIGN PATENT DOCUMENTS

| | | | |
|---|---|---|---|
| EP | 1863901 A1 | 12/2007 | |
| RU | 1365674 A1 | 7/1996 | |
| WO | 9742307 A1 | 11/1997 | |
| WO | 2007009463 A2 | 1/2007 | |
| WO | 2007028811 A1 | 3/2007 | |
| WO | 2007136762 A2 | 11/2007 | |
| WO | 2008119082 A2 | 10/2008 | |
| WO | 2009109631 A1 | 9/2009 | |
| WO | 2009130386 A1 | 10/2009 | |
| WO | 2011161141 A1 | 12/2011 | |
| WO | 2012027279 A1 | 3/2012 | |
| WO | 2012041990 A1 | 4/2012 | |
| WO | 2014105289 A1 | 7/2014 | |
| WO | WO-2015034964 A1 * | 3/2015 | ............... C13K 1/02 |
| WO | 2016025678 A1 | 2/2016 | |
| WO | 2016025679 A1 | 2/2016 | |

OTHER PUBLICATIONS

International Search Report and Written Opinion received for PCT Patent Application No. PCT/US2015/044994, dated Nov. 2, 2015, 8 pages.

International Search Report and Written Opinion received for PCT Patent Application No. PCT/US2015/044990, dated Nov. 2, 2015, 7 pages.

International Search Report and Written Opinion received for PCT Patent Application No. PCT/US2017/058936, dated Feb. 7, 2018, 9 pages.

International Search Report and Written Opinion received for PCT Patent Application No. PCT/US2017/058939, dated Dec. 14, 2017, 8 pages.

International Search Report and Written Opinion received for PCT Patent Application No. PCT/US2017/058951, dated Jan. 2, 2018, 8 pages.

Brown et al., "Fast Pyrolysis and Bio-Oil Upgrading", Biomass-to-Diesel Workshop; Pacific Northwest National Laboratory, Sep. 5-6, 2006.

Zeitsch, "The Chemistry and Technology of Furfural and its Many By-Products", Sugar Series, vol. 13, Feb. 1, 2000, pp. 48-51 and 303-306.

Galbe et al., "A Review of the Production of Ethanol from Softwood", Applied Microbiology and Biotechnology, vol. 59, 2002, pp. 618-628.

Ong, "Conversion of Lignocellulosic Biomass to Fuel Ethanol—A Brief Review", The Planter, vol. 80, Issue No. 941, Aug. 2004, pp. 517-524.

Moller, "Cell Wall Saccharification", Outputs from the EPOBIO Project, Nov. 2006, pp. 1-69.

Mosier et al., "Features of Promising Technologies for Pretreatment of Lignocellulosic Biomass", Bioresource Technology, vol. 96, 2005, pp. 673-686.

Holtzapple et al., "The Ammonia Freeze Explosion (AFEX) process—A Practical Lignocellulose Pretreatment", Applied Biochemistry and Biotechnology, vol. 28/29, Issue No. 1, Mar. 1991, pp. 59-74.

Kumar et al., "Methods for Pretreatment of Lignocellulosic Biomass for Efficient Hydrolysis and Biofuel Production", Industrial & Engineering Chemistry Research, vol. 48, Issue No. 8, 2009, pp. 3713-3729.

Lavarack et al., "The Acid Hydrolysis of Sugarcane Bagasse Hemicellulose to Produce Xylose, Arabinose, Glucose and other Products", Biomass & Bioenergy, vol. 23, Issue No. 5, 2002, pp. 367-380.

Yang et al., "One-Step Catalytic Transformation of Carbohydrates and Cellulosic Biomass to 2, 5 Dimethyltetrahydrofuran for Liquid Fuels", Chem Sus Chem, vol. 3, Issue No. 5, May 25, 2010, pp. 597-603.

Lange et al., "Furfural—A Promising Platform for Lignocellulosic Biofuels", Chem Sus Chem, vol. 5, Issue No. 1, Jan. 9, 2012, pp. 150-166.

Nhien et al., "Design and Optimization of Intensified Biorefinery Process for Furfural Production through a Systematic Procedure", Biochemical Engineering Journal, vol. 116, Apr. 5, 2016, pp. 166-175, XP029805891.

International Search Report and Written Opinion received for PCT Patent Application No. PCT/US2015/044981, dated Nov. 2, 2015, 8 pages.

* cited by examiner

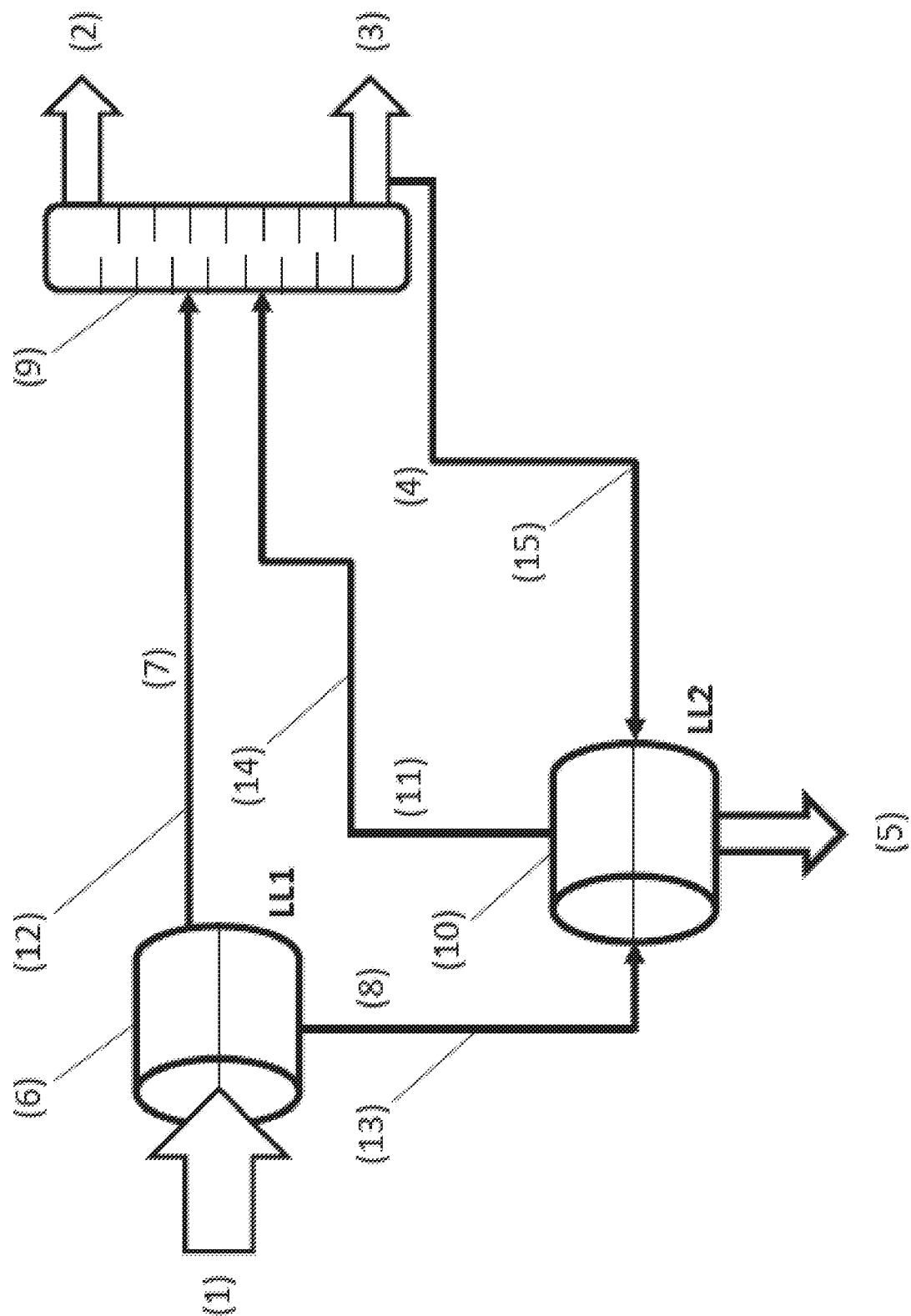

PROCESS FOR THE RECOVERY OF FURFURAL

CROSS REFERENCE TO RELATED APPLICATIONS

This is a national stage application of International Application No. PCT/US2017/058942, filed 30 Oct. 2017, which claims benefit of priority to U.S. Provisional Patent Application No. 62/415,531, filed 1 Nov. 2016.

FIELD OF THE INVENTION

The present invention relates to a process for the high recovery/extraction of furfural from a composition in an energy efficient manner.

BACKGROUND OF THE INVENTION

Furfural is a useful precursor for industrial chemicals, in particular to produce furan and its derivatives.

Furfural may be produced from the hydrolysis of feedstock comprising lignocellulosic biomass. Lignocellulosic biomass comprises mainly hemicelluloses and cellulose, and smaller portions of lignin and protein. Hemicelluloses are a branched polysaccharide of heterogeneous monosaccharide content. Their molecular structure includes the five-carbon monosaccharides ('pentose(s)') xylose and arabinose, as well as the six-carbon monosaccharides ('hexose(s)') mannose, galactose and rhamnose. Due to their xylose and arabinose content, hemicelluloses are a suitable source of monomeric and polymeric pentoses. In comparison, cellulose is a linear-polysaccharide made up of polymerised glucose (a six-carbon monosaccharide/hexose). Compared to cellulose, hemicelluloses are easier to breakdown into their constituent monosaccharides.

Commercially available feedstock comprising lignocellulosic biomass includes bagasse, which is the fibrous matter that remains after sugarcane or sorghum stalks are crushed their juices extracted. An established continuous process for the production of furfural from bagasse is the Rosenlew process, the details of which are discussed in "The Chemistry and Technology of Furfural and its Many By-Products", 1st Edition, K. Zeitsch, pages 48-51 and 303-306.

WO2012041990 describes the production of furfural from bagasse-derived hemicellulose, via its gaseous acid catalysed hydrolysis to pentoses, which are then dehydrated to produce furfural.

WO2016025678 describes the production of furfural, where initially hemicellulose is hydrolysed in a solution comprising α-hydroxysulfonic acid, a portion of the α-hydroxysulfonic acid is then removed from the hydrolysis reaction product to produce an acid-removed stream, and finally the acid-removed stream is subjected to a dehydrating step to produce furfural.

WO2016025679 describes a hydrolysis step, which is buffered to, preferably, less than pH 1, followed by a dehydrating step to produce furfural.

In both WO2016025678 and WO2016025679, during the dehydration reaction step, a "bi-phasic" dehydration reaction mixture is formed by the addition of 'a water-immiscible organic phase' (i.e. a solvent) into the dehydration reaction mixture. The dehydration reaction mixture is then separated into an aqueous product stream, and an organic product stream comprising a portion of furfural. However, WO2016025678 and WO2016025679 do not disclose how furfural can be fully recovered and purified from the organic product stream comprising furfural. Further, WO2016025678 and WO2016025679 do not disclose how furfural remaining in the aqueous product stream can be efficiently recovered and purified from the aqueous product stream.

Solvent extraction of furfural from an aqueous environment is complicated by the carry-over of water into the organic phase, as well as the formation of a furfural-water azeotrope. The extent of the water carry-over depends on the solvent used. Oxygenate solvents, such as those of phenolic compounds, carry more water into the organic phase (approximately around 10,000 ppm to around 40,000 ppm), as compared to aromatic solvents (approximately around 200 ppm to around 1,000 ppm). Further, if furfural is present in an aqueous environment, a furfural-water azeotrope can be formed. It is known in the art of extracting chemical compounds from mixtures of compounds that the presence of any azeotrope increases the energy consumption of a given process, as well as complicating the step and the equipment needed for that process. As aromatic solvents have a lesser tendency to carry-over water, on the face of it the furfural-water azeotrope problem should be less severe; however, due to furfural's properties, aromatic solvents' ability to extract furfural is lower, which potentially decreases the overall furfural recovery.

In the Rosenlew process, furfural is isolated from the reaction mix by azeotropic distillation, and no solvent extraction is used. The Rosenlew process consumes about 10 tonnes of steam to recover each tonne of furfural.

It would, therefore, be advantageous to provide a process for the recovery of furfural that is more energy-efficient than the prior art processes, as well as one which provides a high-yield of furfural.

SUMMARY OF THE INVENTION

Accordingly, the present invention provides a process for a process for the extraction of furfural from a composition comprising furfural, water, at least one acid and an aromatic solvent with a boiling point higher than that of furfural; said process comprising: (a) subjecting the composition to a first liquid-liquid separation step in a first liquid-liquid separator to provide: (i) a first organic phase comprising the aromatic solvent and a portion of the furfural, and (ii) a first aqueous phase comprising the remainder of the furfural and the at least one acid; (b) conveying the first organic phase from step (a) along a first line to a distillation column and subjecting the first organic phase to a distillation step to provide: (i) a top stream comprising furfural, and (i) a bottom stream comprising the aromatic solvent; (c) conveying the first aqueous phase from step (a) and a portion of the bottom stream from step (b) to a second liquid-liquid separator, and subjecting the first aqueous phase from step (a) and the portion of the bottom stream from step (b) to a second liquid-liquid separation step to provide: (i) a second organic phase comprising the aromatic solvent and a portion of the furfural, and (ii) an aqueous waste stream comprising water and the at least one acid; (d) conveying the second organic phase from step (c) along a second line which either feeds its contents into the first line or into the distillation column, and subjecting the resultant mixture to the distillation step of step (b).

BRIEF DESCRIPTION OF THE DRAWING

FIG. 1 shows a simplified schematic diagram of an embodiment of the process according to the invention.

DETAILED DESCRIPTION OF THE INVENTION

The present inventors have surprisingly found that the process for the extraction of furfural according to the present invention provides a higher yield of furfural than known processes, and consumes less energy to produce each tonne of furfural, suitably, by consuming less than 4 tonnes of steam to recover each tonne furfural with a furfural recovery of over 97%.

In the process according to the present invention, furfural is extracted from a composition comprising furfural, at least one acid and an aromatic solvent with a boiling point higher than that of furfural.

In an embodiment of the present invention the composition may be derived from a product stream of a pentose dehydration step, wherein a pentose feed stream is dehydrated.

Suitably, the pentose dehydration step dehydrates a pentose feed stream comprising monomeric and polymeric pentoses, which is derived from a hydrolysis step wherein a lignocellulosic biomass is hydrolysed in the presence of at least one inorganic acid; although as an alternative, other processes may also be used to hydrolyse the lignocellulosic biomass, such as ones which may use basic or neutral pH conditions. Suitably, the lignocellulosic biomass hydrolysis step is as described in WO2016025678 and WO2016025679.

Where used for the hydrolysis of lignocellulosic biomass, suitably, the at least one inorganic acid may be selected from, such as but not limited to, hydrochloric acid, nitric acid, phosphoric acid, boric acid sulphuric acid and α-hydroxysulfonic acid, or combinations thereof.

Suitably, some types of lignocellulosic biomass may intrinsically contain at least one organic acid, or will form at least one organic acid upon being subjected to the hydrolysis. Examples of such acids include, but are not limited to, formic acid, acetic acid, lactic acid, glycolic acid, levulinic acid, oxalic acid and citric acid, or combinations thereof. When using such types of biomass material, the need to add at least one acid inorganic acid may be reduced or even eliminated as the in-situ generated acid may provide the necessary acidic pH.

According to an embodiment of the invention, the composition may be derived from the product stream of a pentose dehydration step; said product stream is also hereinafter referred to as the "dehydration product stream".

Suitably, the pentose dehydration step takes place in a dehydration reaction mixture, where the dehydration of monomeric and polymeric pentoses is catalysed by at least one inorganic acid at an elevated temperature, although at least one organic acid may also take part in such catalysis.

The dehydration reaction mixture comprises the pentose feed stream, at least one inorganic acid, at least one organic acid and furfural; the level of the furfural depending on how long the pentose dehydration step has been running.

The at least one inorganic acid and the at least one organic acid present in the dehydration reaction mixture will have carried through in the pentose feed stream from the hydrolysis step to the pentose dehydration step, where the hydrolysis step precedes the pentose dehydration step.

However, if the hydrolysis step was carried out under basic or neutral pH conditions as an alternative, or if it is determined that the pH of the dehydration reaction mixture is not acidic enough, more inorganic acid may be added to the dehydration reaction mixture.

Preferably, the pentose dehydration step is carried out at the elevated temperature of at least 100° C., more preferably at least 110° C., and even more preferably at least 140° C. Preferably, the pentose dehydration step is carried out at the elevated temperature of at most 250° C., more preferably at most 200° C., and even more preferably at most 150° C.

Preferably, the pentose dehydration step is carried out for a period of at least 1 second, more preferably at least 5 minutes, even more preferably at least 10 minutes and most preferably at least 30 minutes. Preferably, the pentose dehydration step is carried out for a period of at most 24 hours, more preferably at most 12 hours, even more preferably at most 5 hours and most preferably at most 2 hours.

One or more aromatic solvents may be added to the dehydration reaction mixture. The presence of the aromatic solvent in the dehydration reaction mixture creates an aqueous phase and an organic phase.

Preferably, the dehydration reaction mixture to aromatic solvent ratio is at least 1 to 0.05% vol., more preferably said ratio is 1 to 0.1% vol., even more preferably said ratio is 1 to 0.25% vol., most preferably said ratio is 1 to 0.4% vol.

Preferably, the dehydration reaction mixture to aromatic solvent ratio is at most 1 to 2.5% vol., more preferably said ratio is 1 to 1.25% vol., even more preferably said ratio is 1 to 0.75% vol., most preferably said ratio is 1 to 0.6% vol.

Preferably, the aromatic solvent is selected from alkyl benzene compounds of 10 or more carbons, alkyl naphthalene compounds of 10 or more carbons, and from naphthalene.

Preferably, the aromatic solvent is selected from compounds such as, but not limited to, 1-ethyl-2,3-dimethylbenzene, 1-ethyl-2,5-dimethylbenzene, 1-ethyl-2,4-dimethylbenzene, 1-ethyl-3,4-dimethylbenzene, 1,2,3,5-tetramethylbenzene, 1,2,3,4-tetramethylbenzene, 1,2,4,5-tetramethylbenzene, naphthalene, 1-methylnaphthalene, 2-methylnaphthalene, n- and sec-propyl-methyl benzenes (with the methyl group located in 2-,3-,4- or 5-position) n- and sec-butyl benzene and n- and sec-pentyl benzene.

Suitably, the aromatic solvent may be a mixture of one or more of such compounds.

Preferably, the aromatic solvent has a ratio of aromatic carbons to aliphatic carbons of greater than 1. If the aromatic solvent is a pure compound, the ratio of aromatic carbons to aliphatic carbons will be evident to the skilled person. However, if the aromatic solvent is a mixture of one or more of such compounds, a method of determining the ratio of aromatic carbons to aliphatic carbons may be by subjecting the aromatic solvent mixture to $^{13}C$ NMR analysis and obtaining a ratio of the peaks representing the aromatic and aliphatic moieties by techniques known in the art.

The aromatic solvent may be added to the dehydration reaction mixture at the start of, or part way through, the pentose dehydration step.

Suitably, the aromatic solvent may also be added to the dehydration product stream to form the composition, if the pentose dehydration step did not occur in the presence of the aromatic solvent.

However, preferably, the aromatic solvent may be added to the dehydration reaction mixture at the start of the pentose dehydration step. Optionally, the source of the aromatic solvent may be a recycle stream from one or more of steps of the process of the present invention, such stream being recycled as a feed to the pentose dehydration step.

If the aromatic solvent is added to the dehydration reaction mixture at the start of, or part way through, the pentose dehydration step, the formation of furfural takes place in the aqueous phase.

Suitably, the aromatic solvent has selectivity towards furfural over water and over the at least one inorganic acid, and selectively extracts furfural from said aqueous phase into the organic phase as the pentose dehydration step converts the pentose feed stream into furfural.

The aromatic solvent also has selectivity towards furfural over the at least one organic acid, however a small amount of at least one organic acid may partition into the organic phase depending on how much water any given aromatic solvent may carry over; such small amount is deemed to have insignificant consequence in the process of the present invention.

Therefore the amount of furfural in the organic phase varies depending on how far the pentose dehydration step has progressed.

Suitably, the aromatic solvent provides at least three advantages.

Firstly, compared to, for example, oxygenate solvents, the aromatic solvent carries-over less water into the organic phase, and therefore suitably the aromatic solvent does not extract any of the at least one organic acid and any significant amount of at least one inorganic acid into the organic phase. This has the advantage that by selectively extracting the furfural into the organic phase, furfural is removed from the presence of such acids, and therefore any undesired loss of furfural via degradation and/or oligomerisation reactions that may be taking place during the pentose dehydration step are prevented, and therefore furfural yield is improved.

Secondly, again due to the aromatic solvent carrying less water into the organic phase, no furfural-water azeotrope can be formed in the organic phase, which simplifies the separation of furfural from the organic phase of the pentose dehydration step.

Thirdly, because the boiling point of water at ambient pressure is lower than the boiling point of furfural at ambient pressure (about 100° C. versus about 161° C., respectively) extraction of the furfural from the dehydration reaction product stream reduces the need to boil-off significant amount of water to purify the furfural from water. Instead, because the aromatic solvent has a boiling point higher than that of furfural, furfural can be distilled off from the aromatic solvent, and since the quantity of furfural in the aromatic solvent is only a fraction per unit volume of the aromatic solvent, in processes such as distillation, a lesser quantity of material (i.e. the furfural with its lower boiling point) needs to be boiled off. Suitably, this provides an energy advantage (saving).

FIG. 1 shows a simplified schematic diagram of an embodiment of process according to the invention, illustrating that a composition (1) is supplied to a first liquid-liquid separator (6), which provides a first organic phase (7) comprising the aromatic solvent and a portion of the furfural, which is conveyed along a first line (12) to a distillation column (9).

A first aqueous phase (8), also provided by the first liquid-liquid separator (6) and comprising the remainder of the furfural and the at least one acid is conveyed along a line (13) to a second liquid-liquid separator (10).

The distillation column (9) provides a top stream comprising furfural (2), and a bottom stream comprising the aromatic solvent (3).

A portion bottom stream (3) comprising the aromatic solvent also may be conveyed along a line (13) to the second liquid-liquid separator (10).

The second liquid-liquid separator (10) provides a second organic phase (11) comprising the aromatic solvent and a portion of the furfural, which is conveyed along a second line (14) to the distillation column (9).

The second liquid-liquid separator (10) provides an aqueous waste stream comprising water and at least one acid (5).

In the process according to the present invention, furfural is extracted from a composition comprising furfural, at least one acid and an aromatic solvent with a boiling point higher than that of furfural.

To commence the extraction of furfural from the composition, the composition is subjected to a first liquid-liquid separation step in a first liquid-liquid separator (6) to provide: (i) a first organic phase (7) comprising the aromatic solvent and a portion of the furfural, and (ii) a first aqueous phase (8) comprising the remainder of the furfural and the at least one acid.

Preferably, the first liquid-liquid separation (6) may be operated at a temperature of at most 200° C., more preferably at a temperature of at most 180° C., even more preferably at a temperature of at most 160° C., even more preferably at a temperature of at most 150° C., so long as the liquid separates into two phases at the separation temperature.

Preferably, the first liquid-liquid separation (6) may be operated at a temperature of at least ambient temperature, more preferably at a temperature of at least 60° C., even more preferably at a temperature of at least 100° C., even more preferably at a temperature of at least 130° C., so long as the liquid separates into two phases at the separation temperature.

The first liquid-liquid separation step is carried out in any suitable liquid-liquid separator as would be known to the person skilled in the art.

Prior to undergoing the first liquid-liquid separation step, the composition may optionally be routed through a, preferably solid/liquid, separation step, to remove any insoluble humins or other tar that may have been formed during the dehydration step, and which may otherwise negatively interfere with the separation of the organic phase from the aqueous phase, or the later separation or purification steps. Formation of humins and/or tar is a well-known problem associated with the production of bio-based products. Humins are dark, amorphous and undesirable acid by-products and resinous material resulting from sugars, and other organic compound degradation. Tar is a generic reference to organic material which is insoluble in water, which is dark in colour, and which tends to become viscous and very dark to almost black when concentrated.

In the process of the present invention, the first organic phase provided by the first liquid-liquid separation step is conveyed along a first line (12) to a distillation column (9) and subjected to a distillation step to provide: (i) a top stream (2) comprising furfural, and (ii) a bottom stream (3) comprising the aromatic solvent.

Furfural has a boiling point at ambient pressure of about 161° C., and as the aromatic solvent has a boiling point higher than that of furfural, a top stream (2) comprising furfural is obtained. Suitably, the greater the difference between the boiling point of furfural and the aromatic solvent, the easier and cleaner the separation between these compounds will be.

Suitably the aromatic solvent may be 1-methylnaphthalene, which has a boiling point of about 242° C. at ambient pressure, and suitably this gives sufficient difference in respective boiling points to achieve 100% furfural purity.

Suitably, the distillation step may be a vacuum distillation step. Suitably, the vacuum column may be operated at a pressure of around 0.00133 MPa (10 mmHg) to lower the boiling point of furfural from about 161° C. Suitably, under such conditions, a top stream comprising furfural, and a bottom stream comprising the aromatic solvent are obtained. Advantageously, the vacuum distillation step overcomes the possibility of furfural loss from heat-induced degradation and oligomerisation.

Suitably, the distillation step may be an atmospheric distillation step, where suitably, furfural can be obtained as the top stream in the region of the distillation column at a temperature of about 160° C. to about 180° C., leaving a bottom stream comprising the aromatic solvent.

Suitably, although the aromatic solvent has a preferred selectivity towards furfural, during the first liquid-liquid separation step, a portion of the furfural may nevertheless remain in the aqueous phase of the composition. The amount of furfural present in the aqueous phase may depend on which aromatic solvent is used, however it may be up to about 60% of the amount of furfural that is present in the composition. This is undesirable, as it may lead to furfural loss, for example, due to degradation and/or oligomerisation of the furfural remaining in the aqueous phase by reacting with other components present in the aqueous phase. It is further undesirable as furfural remaining the aqueous phase forms an azeotrope with water. This complicates the separation of furfural from aqueous phase because the boiling point of the furfural-water azeotrope at ambient pressure is about 98° C., this being very close to the boiling point of water from which it needs to be separated from.

Following the first liquid-liquid separation step, in order to achieve both high furfural recovery and high furfural purity, furfural needs to be recovered efficiently from both the first organic phase (7) (comprising the aromatic solvent and a portion of the furfural) and from the first aqueous phase (8) (comprising the remainder of the furfural and the at least one acid). Further, furfural has to be extracted efficiently from the furfural-water azeotrope.

Therefore, to achieve overall high furfural recovery, high furfural purity and energy efficiency, the inventors have introduced a second liquid-liquid separation step into the process of the present invention, which increases extraction of furfural from the first aqueous phase by a more efficient use of the aromatic solvent.

To achieve this, a second liquid-liquid separator (10) is supplied with the first aqueous phase (8) exiting the first liquid-liquid separation step (which comprises the remainder of the furfural and the at least one acid, the furfural being mainly in the form of a furfural-water azeotrope), and the second liquid-liquid separator (10) is also supplied with a portion of the bottom stream (4) from the distillation step (which comprises the aromatic solvent). By feeding these two streams into the second liquid-liquid separator (10), the aromatic solvent can be further utilised to extract more furfural from the remainder of the furfural left in the aqueous phase (8).

Therefore in the process of the present invention, a portion of the bottom stream (4) from the distillation step and the first aqueous phase (8) from the first liquid-liquid step are conveyed to a second liquid-liquid separator (10), and subjected to a second liquid-liquid separation step to provide: (i) a second organic phase (11) comprising the aromatic solvent and a portion of the furfural, and (ii) an aqueous waste stream (5) comprising the at least one acid.

Suitably, at least about 5% vol. of the bottom stream from the distillation step is conveyed to the second liquid-liquid separator (10). Such amount may be preferably at least about 10% vol., more preferably at least about 25% vol., even more preferably at least about 30% vol., and most preferably at least about 50% vol. Suitably, at most about 80% vol. of the bottom stream from the distillation step is conveyed to the second liquid-liquid separator (10). Such amount may be preferably at most about 70% vol., more preferably at most about 65% vol., even more preferably at most 60% vol., and most preferably at most 55% vol.

Suitably, the remainder of the solvent which is not conveyed to the second liquid-liquid separator (10) may be fed into the pentose dehydration step.

Preferably, the second liquid-liquid separation may be operated at a temperature of at most 120° C., more preferably at a temperature of at most 100° C., even more preferably at a temperature of at most 80° C., even more preferably at a temperature of at most 60° C., so long as the liquid separates into two phases at the separation temperature.

Preferably, the second liquid-liquid separation may be operated at a temperature of at least ambient temperature, more preferably at a temperature of at least 30° C., even more preferably at a temperature of at least 40° C., even more preferably at a temperature of at least 50° C., so long as the liquid separates into two phases at the separation temperature.

In the process of the present invention, following the second liquid-liquid separation step, the second organic phase (11) (comprising the aromatic solvent and a portion of the furfural originating from the second liquid-liquid separator) is conveyed along a second line (14), which either feeds its contents into the first line (12) or into the distillation column (9), and subjecting the resultant mixture to the distillation step previously described.

Suitably, feeding the contents of the second line (14) into the first line may provide better mixing of the first organic phase (7) and the second organic phase (11), before they enter into the distillation column (9) to undergo the distillation step. Alternatively, the second line (14) may convey the second organic phase (11) directly into the distillation column to undergo the distillation step.

In another embodiment, each of the first organic phase (7) and the second organic phase (11) are fed separately into different distillation trays of the distillation column (9), depending on their respective concentration of furfural. Suitably, the phase with the lower furfural concentration is fed into a lower tray than the phase with the higher furfural concentration.

The recycling of the aromatic solvent through the second liquid-liquid separator (10) provides both energy efficiency for the process overall, as well as increasing the utility of the aromatic solvent.

Optionally, in one embodiment, the bottom stream (4) from the distillation step comprising the aromatic solvent may be recycled as a feed to the pentose dehydration step.

During the second liquid-liquid separation step, an aqueous waste stream (5) is produced. The aqueous waste stream comprises at least one acid. Suitably, the aqueous waste stream comprises other compounds that the aromatic solvent was not able to extract, including water and optionally a residual portion of furfural, which may account to about less than 1% loss of the overall furfural yield.

Optionally, the aqueous waste stream (5) of the second liquid-liquid separation step (c) comprising water and the at least one acid may be recycled as a feed to the hydrolysis step.

Although in the process of the present invention the inventors have sought to obtain maximum furfural yield, in the interest of energy efficiency, suitably the inventors have not tried to recover the less than 1% loss of the overall furfural yield. Instead, in the pursuit for energy efficiency, suitably, the waste stream (5) may be recycled to feed the hydrolysis step to benefit from its at least one acid content, as well as from the temperature of this stream as compared to the fresh supply to the pentose dehydration step of water and at least one acid at ambient temperature.

Examples

A process line up, as depicted in FIG. 1, was assessed for furfural recovery using process modelling Aspen plus (Version 7.3) software licensed from Aspen Technology Inc., MA.

The modelled process line up is representative of a furfural separation scheme from a process stream containing furfural on a furfural manufacturing plant.

The results obtained in this example are representative of expected furfural recovery rates, fraction of furfural recovery from feed stream, furfural purity, heat duty (MW), and steam usage measured in tonne of steam/tonne of furfural produced.

Thermodynamic data contained in 'NRTL-HOC property method' set was used in this simulation.

Steam consumption in the process line up was determined on the basis of using 4.48 MPa high pressure steam.

The feed stream, the composition (1), contains water, furfural, acetic acid (as the at least one organic acid), 1-methyl naphthalene (1-MNP) (representative of an aromatic solvent with a boiling point higher than that of furfural).

The process of the present invention enables separation of furfural from the composition with high purity and allows for recycle of solvent for re-use in the process.

Table 1 present all the process stream data output.

Table 2 and 3 give process operating conditions and results summary for distillation column (9) and liquid-liquid separators (6 and 10) used in the process line-up.

Table 4 presents the summary of results for furfural separation scheme.

Based on the simulation output this separation process line up consumes about 3.8 tonne steam/tonne furfural produced. This is about 62% reduction in steam usage compared to consumption of 10 tonne steam/tonne furfural produced in the state-of-the-art Rosenlew's process for commercial furfural production.

TABLE 1

Stream Summary Results

| Component Mass Flow | | Stream # | | | | | | |
|---|---|---|---|---|---|---|---|---|
| | | 3 | 4 | 5 | 11 | 2 | 1 | 7 | 8 |
| Water | TONNE/DAY | 0 | 0 | 14365 | 0 | 0 | 14365 | 0 | 14365 |
| FURFURAL | TONNE/DAY | 0 | 0 | 18 | 159 | 613 | 631 | 454 | 177 |
| Acetic Acid | TONNE/DAY | 0 | 0 | 240 | 0 | 0 | 240 | 0 | 240 |
| 1-MNP | TONNE/DAY | 7182 | 3585 | 0 | 3585 | 0 | 7182 | 7182 | 0 |
| Mass Flow | TONNE/DAY | 7182 | 3585 | 14623 | 3744 | 614 | 22418 | 7636 | 14782 |
| Temperature | C. | 244 | 244 | 100 | 100 | 161 | 90 | 90 | 90 |

TABLE 2

Distillation Column Summary

| | Units | D1 |
|---|---|---|
| Pressure | MPa | 0.1 |
| Reflux Ratio | | 1 |
| Distillate Rate | tonne/day | 613.5 |
| Number of trays | | 25 |
| Feed rate | tonne/day | 11380 |
| Reboiler Temperature | C. | 244 |
| Reboiler Duty | MW | 46 |
| Steam usage (4.48 MPa) | tonne/day | 2353 |

TABLE 3

Liquid-Liquid Separator Summary

| | Units | LL1 | LL2 |
|---|---|---|---|
| Pressure | MPa | 0.1 | 0.1 |
| Temperature | C. | 90 | 90 |
| Feed rate | tonne/day | 22418 | 18367 |

TABLE 4

Separation Scheme Results Summary

| | Units | |
|---|---|---|
| Furfural Recovery Rate | tonne/day | 613.3 |
| Furfural Recovery | | 97.2% |
| Furfural Purity | | 100% |
| Total energy requirement | MW | 46 |
| Steam Usage (650 psig) | tonne/day | 2353 |
| Steam Consumption | t/t FUR produced | 3.8 |

That which is claimed is:

1. A process for the extraction of furfural from a composition (1) comprising an aromatic solvent and a dehydration reaction mixture comprising furfural, water, and at least one acid, wherein the aromatic solvent has a boiling point higher than that of furfural, said process comprising:
   (a) subjecting the composition (1) to a first liquid-liquid separation step in a first liquid-liquid separator (6) to provide:
      a first organic phase (7) comprising the aromatic solvent and a portion of the furfural, and
      a first aqueous phase (8) comprising the remainder of the furfural and the at least one acid;
   (b) conveying the first organic phase (7) from step (a) along a first line (12) to a distillation column (9) and subjecting the first organic phase (7) to a distillation step to provide:

a top stream (2) comprising furfural, and a bottom stream (3) comprising the aromatic solvent;

(c) conveying the first aqueous phase (8) from step (a) and a portion of the bottom stream (4) from step (b) to a second liquid-liquid separator (10), and subjecting the first aqueous phase (8) from step (a) and the portion of the bottom stream (4) from step (b) to an extraction step to provide:

a second organic phase (11) comprising the aromatic solvent and a portion of the furfural, and an aqueous waste stream (5) comprising water and the at least one
acid;

(d) conveying the second organic phase (11) from step (c) along a second line (14) which either feeds its contents into the first line (12) or into the distillation column (9) and subjecting the resultant mixture to the distillation step of step (b), wherein the dehydration reaction mixture to aromatic solvent ratio is from at least 1 to 0.05% vol to at most 1 to 2.5% vol.

2. The process according to claim 1, wherein the composition (1) is derived from a product stream of a pentose dehydration step wherein a pentose feed stream is dehydrated.

3. The process according to claim 2, wherein the pentose feed stream is derived from a hydrolysis step wherein a lignocellulosic biomass is hydrolysed.

4. The process according to claim 2, wherein a portion of the bottom stream (3) of step (b) comprising the aromatic solvent is recycled as a feed to the pentose dehydration step.

5. The process according to claim 2, wherein the aqueous waste stream (5) of step (c) comprising water and the at least one acid is recycled as a feed to the hydrolysis step.

6. The process according to claim 1, wherein the aromatic solvent has a ratio of aromatic carbons to aliphatic carbons of greater than 1.

7. The process according to claim 1, wherein the aromatic solvent is selected from the group consisting of 1-ethyl-2,3-dimethylbenzene, 1-ethyl-2,5-dimethylbenzene, 1-ethyl-2,4-dimethylbenzene, 1-ethyl-3,4-dimethylbenzene, 1,2,3,5-tetramethylbenzene, 1,2,3,4-tetramethylbenzene, 1,2,4,5-tetramethylbenzene, naphthalene, 1-methylnaphthalene, 2-methylnaphthalene, n- and sec-propyl-methyl benzenes, n- and sec-butyl benzene and n- and sec-pentyl benzene, or any combination thereof.

8. The process according to claim 1, wherein the distillation step is an atmospheric distillation step, or is a vacuum distillation step.

9. The process according to claim 1, wherein the first liquid-liquid separation step is operated at a temperature range of from ambient temperature to 200° C.

10. The process according to claim 1, wherein the second liquid-liquid separation step is operated at a temperature range of from ambient temperature to 120° C.

* * * * *